United States Patent
Joseph et al.

(10) Patent No.: US 12,360,448 B2
(45) Date of Patent: Jul. 15, 2025

(54) VISUALIZATION SYSTEM HAVING OPTIMIZED DEFLECTION PRISM

(71) Applicant: Scholly Fiberoptic GmbH, Denzlingen (DE)

(72) Inventors: Hannes Joseph, Bahlingen (DE); David Hensle, Freiburg (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 148 days.

(21) Appl. No.: 18/469,940

(22) Filed: Sep. 19, 2023

(65) Prior Publication Data

US 2024/0094617 A1 Mar. 21, 2024

(30) Foreign Application Priority Data

Sep. 21, 2022 (DE) .......................... 102022124306.0

(51) Int. Cl.
| | |
|---|---|
| *A61B 1/00* | (2006.01) |
| *A61B 1/05* | (2006.01) |
| *G02B 5/04* | (2006.01) |
| *G03B 35/08* | (2021.01) |
| *H04N 13/239* | (2018.01) |
| *H04N 23/50* | (2023.01) |
| *H04N 23/55* | (2023.01) |

(52) U.S. Cl.
CPC .......... *G03B 35/08* (2013.01); *A61B 1/00194* (2022.02); *A61B 1/05* (2013.01); *H04N 13/239* (2018.05); *H04N 23/55* (2023.01); *H04N 23/555* (2023.01)

(58) Field of Classification Search
CPC ....... G03B 35/08; A61B 1/00194; A61B 1/05; A61B 1/042; A61B 1/051; A61B 1/00193; A61B 1/00096; H04N 13/239; H04N 23/55; H04N 23/555
See application file for complete search history.

(56) References Cited

U.S. PATENT DOCUMENTS

| | | | | |
|---|---|---|---|---|
| 9,661,990 | B2* | 5/2017 | Hofer | A61B 1/00193 |
| 10,292,574 | B2* | 5/2019 | Tuscher | A61B 1/00179 |
| 10,441,138 | B2* | 10/2019 | Zhao | A61B 1/042 |

(Continued)

FOREIGN PATENT DOCUMENTS

| | | |
|---|---|---|
| DE | 102020129739 | 5/2022 |
| DE | 102020132951 | 6/2022 |

*Primary Examiner* — Howard D Brown, Jr.
(74) *Attorney, Agent, or Firm* — Volpe Koenig

(57) ABSTRACT

For improved imaging in a visualization system (1) having two image sensors (2a, 2b), which are spaced apart from one another axially with respect to a longitudinal axis (27) of the visualization system (1) and sensorially acquire a respective imaging beam path (4a, 4b), which is generated by an assigned imaging optical unit (31) upstream of a deflection prism (3), it is provided that a structural height of the prism (3) be made suboptimal, in order to thus be able to alleviate imaging errors upon use of a wavelength-selective first mirror surface (8) of the prism (3). Moreover, it is alternatively or additionally provided that two optical channels (16a) and (16b) be formed by the imaging optical unit (31), through which the image sensors (2a) and (2b), preferably in different wavelength ranges, can each acquire images of an object (37) observed using the visualization system (1) from different perspectives.

20 Claims, 4 Drawing Sheets

(56) References Cited

U.S. PATENT DOCUMENTS

| | | | |
|---|---|---|---|
| 2013/0250061 A1* | 9/2013 | Hofer | A61B 1/00193 |
| | | | 348/45 |
| 2014/0357951 A1* | 12/2014 | Muller | A61B 1/055 |
| | | | 600/111 |
| 2015/0148630 A1 | 5/2015 | Meester | |
| 2016/0345804 A1* | 12/2016 | Wieters | G02B 23/02 |
| 2019/0265459 A1* | 8/2019 | Hirata | A61B 1/0669 |
| 2022/0070348 A1* | 3/2022 | Breese | H04N 23/73 |
| 2024/0094617 A1* | 3/2024 | Joseph | A61B 1/00096 |

* cited by examiner

VISUALIZATION SYSTEM HAVING OPTIMIZED DEFLECTION PRISM

CROSS-REFERENCE TO RELATED APPLICATIONS

This application claims priority to German Patent Application No. 10 2022 124 306.0, filed Sep. 21, 2022, which is incorporated herein by reference as if fully set forth.

TECHNICAL FIELD

The invention relates to a visualization system, which can be designed in particular as a chip-in-tip (CIT) endoscope, thus in particular as an endoscope having at least one image sensor that is arranged in a distal end region of an endoscope shaft of the endoscope. The visualization system comprises a proximal image sensor, a distal image sensor, and at least one prism. In this case, the prism deflects a first imaging beam path onto the proximal image sensor and a second imaging beam path onto the distal image sensor.

BACKGROUND

Such visualization systems are previously known in the form of endoscopes, in which the two image sensors are arranged in a distal end region of the endoscope. In this case, the image sensors are typically used to detect different wavelength ranges (such as white light and infrared light), wherein these spectral components are separated by a mirror surface in the prism and thus deflected onto the respective image sensor. Furthermore, using dichroic mirrors for such a wavelength-selective deflection is also known.

In such an approach, an imaging optical unit is typically connected upstream from the deflection prism, which defines a specific focal plane that has to correspond to the active sensor surfaces of the image sensors so that sharp imaging can be obtained. Therefore, in this approach both imaging beam paths which extend through the prism are typically designed so that they offer the desired optical path length and do so in consideration of the chromatic longitudinal aberration (which has an effect on the location of the respective focal plane, depending on the wavelength range), so that the respective focal planes come to rest on the respective sensor.

SUMMARY

Proceeding from this previously known prior art, the invention is based on the object of providing a visualization system which, with a small structural size, in particular with respect to the dimensions of the prism, enables a high imaging quality on each of the two image sensors.

To achieve this object, a visualization system with one or more of the features disclosed herein is provided, in particular in an endoscope. In particular, it is therefore provided according to the invention to achieve the object in a visualization system of the type mentioned at the outset that the second imaging beam path, after entry into the at least one prism through a distal entry surface of the prism, is deflected by means of a first reflection on a wavelength-selective first mirror surface of the prism and exits from a distal exit surface of the prism, which is formed on a base side of the at least one prism. Furthermore, it is provided that for a ratio of a length L1 of the base side of the prism and a height H1 of the entry surface, the following applies: $L1/H1 > 1.5$.

Such a visualization system can be used, for example, in medicine or for industrial applications, such as in the inspection of cavities which are difficult to access. If the visualization system is designed as a chip-in-tip (CIT) endoscope (in which the respective image sensor is thus arranged in the endoscope tip), the two image sensors can preferably be arranged in a distal end region of the endoscope.

The length L1 of the base side of the prism can just correspond here to the minimum distance between the first mirror surface and the entry surface, measured along the base side (which can preferably extend parallel to the longitudinal axis of the endoscope/to the optical axis of the first imaging beam path). The total length L2 of the prism, in contrast, can correspond to the maximum distance between the first mirror surface and the entry surface (measured along said optical axis of the first imaging beam path).

The height H1 can preferably be measured here perpendicular to the base side and perpendicular to an optical axis of the first imaging beam path. Moreover, the distal exit surface can even directly adjoin the distal entry surface and/or extend perpendicularly thereto. Embodiments of the prism are particularly preferred in which the following applies: $L1/H1 > 2.0$ or even $L1/H1 > 2.2$.

Various boundary conditions are to be taken into consideration in the design of the prism: In particular, the size of the entry window is to be as large as possible for a given installation space in order to enable good illumination of the image sensors and/or to be able to use large and thus high-resolution image sensors. At the same time, the prism is to remain as small as possible in its structural height, in order to also be able to be used in cramped installation spaces. Finally, the volume of the prism as a whole is to remain small, so that it is manufacturable cost-effectively. This relates in particular to the overall height H1+H2, which the prism forms transversely to the optical axis of the first imaging beam path, wherein H2 is the difference between the height of the entry window and the total height of the prism.

However, the invention has now recognized that it can be reasonable to deviate from a structural form of the prism which results in a minimal overall height. It is therefore possible to optimally ensure the following three boundary conditions as a whole: (1) greatest possible height H1 of the entry window of the prism; (2) least possible overall height H1+H2 of the prism; (3) smallest possible tilt angle of the first mirror surface in relation to the main beam of the first imaging beam path.

This is because, as will be explained in more detail, it is favorable for a high quality of the image which is recorded using the distal image sensor if the first mirror surface is only slightly tilted in relation to the optical axis of the first imaging beam path. This is because in this case in particular peripheral beams of the second imaging beam path are incident comparatively steeply on the first mirror surface. This is advantageous to minimize optical path length differences within the second imaging beam path, from which significant aberrations can arise, which have a negative effect on the imaging, as will be explained in more detail on the basis of a drawing.

In particular if typical image sensors having a respective image format of 16:9 are used, such a design of the prism can offer advantages, in particular if the visualization system comprises two optical channels which are acquired using the image sensor.

The first mirror surface of the prism therefore functions as a beam splitter and divides a beam path incident through the entry window into the first and second imaging beam path.

The first imaging beam path can exit from the at least one prism, for example, from a proximal exit surface which is opposite to the distal entry surface. It is advantageous in this case if the exit surface offers at least the same height H1 as the distal entry surface, so that all light of the first imaging beam path which passes through the entry surface can also be conducted to the proximal image sensor.

The entry surface can in particular make up the entire front surface of the prism, which faces toward the two imaging beam paths. However, the entire entry surface does not have to be penetrated by the two imaging beam paths in this case, rather only a smaller (in particular rotationally-symmetrical) entry window within the entry surface can be penetrated by imaging light beams (while the entry window itself can have a rectangular geometry). It is apparent that therefore the first imaging beam path can also enter the prism through the distal entry surface, in particular through the identical entry window.

The terms "distal" and "proximal" can be understood in relation to the user who uses the visualization system in order to perform image recordings in a specific viewing direction: If the viewing direction points away from the body of the user, the proximal image sensor is located close to the body and the distal image sensor is located far from the body of the user, i.e., the latter is located in the tip of the endoscope.

The at least one prism can preferably (in particular in each case) be designed as a pentaprism (thus having five corners). If two parallel optical channels are formed, the visualization system can also include two prisms, which are in particular arranged separately or are separate from one another, and which are each designed as described above. Or a common prism is used for both channels.

The first imaging beam path can preferably be aligned along a longitudinal axis of the endoscope and can pass the prism without any deflection in transmission. Accordingly, a surface normal of the first image sensor can extend parallel to this longitudinal axis.

Since the first mirror surface can coincide with the proximal exit surface, a main beam of the first imaging beam path can form an angle to a surface normal of the proximal exit surface of the prism. This resulting angle is to be comparatively small according to the invention so that the angle of incidence (measured in relation to the surface normal) of the main beam remains small and therefore also peripheral beams are still incident comparatively steeply on the first mirror surface of the prism.

The surface normal of the distal exit surface (through which the second imaging beam path leaves the prism), in contrast, can be aligned transversely, in particular perpendicularly, to the longitudinal axis of the endoscope or to the optical axis of the first imaging beam path.

The second imaging beam path can therefore preferably be deflected or reflected twice by the prism. The second imaging beam path can initially be deflected in this case on an inner mirror surface of the prism by means of a first reflection, preferably such that the second imaging beam path then propagates counter to the direction of the first imaging beam path.

By means of a second, in particular outer, mirror surface of the prism, the second imaging beam path can then be deflected again by means of a second reflection, in particular such that a main beam of the second imaging beam path extends transversely, preferably perpendicularly, to the longitudinal axis of the endoscope after the second reflection. It is preferred in this case if a main beam of the second imaging beam path exits from the prism parallel to a surface normal of the distal exit surface of the prism. The second mirror surface can preferably be arranged here outside an axial projection of the entry window (along the longitudinal axis of the endoscope). This is because in this case the mirror surface does not conceal the entry window.

Such a visualization system can be designed, for example, as an endoscope having a straight-ahead view or as an oblique view endoscope (for example, using an optical deflection unit, for example in the form of a further prism even before the actual deflection prism). In both cases, however, the respective imaging beam path, possibly after first deflection in the further prism, even before entry into the deflection prism designed according to the invention, can extend in the direction of a longitudinal axis of the endoscope.

The active surface of the respective image sensor can (in each case) be arranged, in particular directly, on the respective exit surfaces of the prism or spaced apart therefrom (thus using an air gap or an intermediate layer, in particular a transparent adhesive layer).

To achieve the object mentioned at the outset and in particular to expand the possible applications of the visualization system and/or enhance its functionality, alternatively or additionally to the above-mentioned features, the additional features are provided, which possibly have independent inventive quality. In particular, it is therefore provided in the visualization system mentioned at the outset that the visualization system includes a left optical channel and a right optical channel for generating 3D images, thus in particular for stereoscopic vision. These two channels can in particular be optically separated from one another, for example by means of an opaque partition layer or an optical barrier. Furthermore, it is provided that the at least one prism (in each case) deflects one or both of the optical channels both onto the proximal image sensor and onto the distal image sensor. This is because in this way in particular 3D images and/or stereoscopic images can be recorded using each of the two image sensors. In this case, the images can be recorded in particular in two different wavelength ranges. For example, one of the two image sensors, in particular the distal image sensor, can be configured for fluorescence imaging, while the other image sensor, thus in particular the proximal image sensor, can be configured for white light imaging. This is because if a first mirror surface as described above is used, these different wavelength ranges can be divided by the prism into the two above-explained imaging beam paths.

The two optical channels can preferably be formed optically and/or spatially separated from one another, in particular such that imaging beams of the left optical channel do not overlap with those of the right optical channel. In particular separate rod lenses can be used for this purpose, which are arranged adjacent to one another, in particular parallel to one another, in order to form the respective imaging beam path of the left or right optical channel.

The features of this second approach can advantageously also be combined with the above-explained features of the first approach.

According to the invention, the object can also be achieved by further advantageous embodiments according to the dependent claims, which are explained hereinafter and can each be combined with all above-explained features:

For example, the visualization system can include two separate distal lens arrangements, which respectively form the mentioned left or right optical channel. These lens arrangements or these two optical channels can also be optically separated from one another, for example by means of an opaque partition layer or an optical barrier. Alternatively thereto, a common distal lens arrangement can also be provided which forms both optical channels (left+right optical channel).

Furthermore, it is possible that in the visualization system a common prism for both optical channels respectively deflects the first imaging beam path onto the proximal image sensor and the second imaging beam path onto the distal image sensor (in each case for each of the two optical channels). However, it is also possible just as well that two separate prisms are used, specifically in each case for one of the two optical channels. In this case, each of these two prisms deflects the first imaging beam path onto the proximal image sensor and the second imaging beam path onto the distal image sensor in each case. This is because two different wavelength ranges can also be separated from one another using these approaches and can thus each be sensorially acquired by the two image sensors.

As already explained above, it has proven to be advantageous if the beams of the second imaging beam path are incident comparatively steeply on the wavelength-selective first mirror surface, because then imaging errors can be avoided and thus a high quality image can be obtained in the second imaging beam path or on the distal image sensor.

One particularly preferred embodiment provides that a surface normal of the first mirror surface of the prism encloses an angle $\alpha$ with an optical axis of the first imaging beam path, for which the following applies $\alpha<20°$. Preferably $\alpha<18°$ or even $\alpha<15°$ can apply.

Depending on how large the bandwidth of the wavelength spectrum to be reflected by the first mirror surface is, the angle $\alpha$ can even be selected as less than $13°$, in particular less than $12°$. In this case, the angle $\alpha$ is to be selected smaller the larger the bandwidth of wavelengths is, since then certain optical path length differences are not to be avoided already in any case (because of the dispersion of the optical elements).

A suboptimal structural height H1+H2 of the prism transverse to the optical axis, which then results as larger than actually necessary, does result from such a small tilt of the first mirror surface in relation to the optical axis of the first imaging beam path. This is because a minimal structural height of the prism is only achieved for the case that the beams are incident both on the first mirror surface and on the second mirror surface at angles $\alpha=\beta=22.5°$ (wherein then also the desired beam deflection by $2\alpha+2\beta=90°$ is achieved). However, the quality of the imaging using the distal image sensor can thus be improved, in particular if the wavelength spectrum and/or the angle spectrum of the light beams incident on the first mirror surface is not insignificantly broad, because at excessively large angles $\alpha$, there is the risk of optical aberrations (chromatic aberrations and astigmatism).

For $\alpha=22.5°$, the resulting overall structural height H1+H2 of the prism would therefore be minimal and at the same time it could already be ensured at a length of the base side of L1=H1 that the beams reflected on the second mirror surface do not strike the first mirror surface again. The longer design of the length L1 of the base side according to the invention offers the advantage here, however, that the angle $\alpha$ can accordingly be selected to be smaller, by which it becomes significantly simpler to ensure small optical path length differences and thus a high imaging quality for a given angle spectrum of light beams incident on the first mirror surface and for an associated wavelength spectrum of reflected beams. It is to be taken into consideration in this case that the angle spectrum which is incident on the first mirror surface can only be reduced sufficiently strongly that greater tilt angles $\alpha$ would also be acceptable with a high level of technical expenditure (i.e., using numerous optical elements). The invention therefore proposes a specific design approach here, which results in a high imaging quality, sufficient illumination, and an acceptable structural height of the prism and at the same time also can be used at very large viewing angles of the visualization system (such as field of view >65°), using dichroic mirrors available on the market. Moreover, the number of required optical elements is kept small, which is advantageous for installation space, weight, and costs.

It can therefore be provided in particular that the proximal image sensor sensorially acquires a first wavelength range and the distal image sensor sensorially acquires a second wavelength range deviating from the first wavelength range. In this case, the first mirror surface can transmit the first wavelength range and reflect the second wavelength range. It is apparent that the two image sensors can also differ in their respective spectral sensitivity, in particular due to different filters on the pixel level.

The first mirror surface can thus pass on the first wavelength range to the proximal image sensor (these wavelengths pass the first mirror) and the second wavelength range to the distal image sensor (these wavelengths are reflected by the mirror).

The first mirror surface can be designed as a dichroic mirror for this purpose. Dichroic mirrors are understood in optics as interference filters which have a different transmittance or reflectance for different wavelength ranges. They typically consist of a sequence of multiple dielectric layers having different indices of refraction, which are applied to a glass substrate (the glass body of the prism here). The design of the dichroic surface and thus the spectral edge sharpness of the dichroic filter for separating the wavelengths is decisive for the function of the first mirror surface. Two factors are important here: (i) The "bandwidth" of angles of incidence which have to be conducted through the prism. The smallest possible difference between main beam and outside beam is desired here, which results in the goal specification of the smallest possible opening angle of the imaging optical unit. However, the number of optical elements used sets limits here. (ii) The tilt angle of the dichroic surface in relation to the main beam of the first imaging beam path or to the longitudinal axis of the endoscope. This is to be minimal because at greater tilt angles of the dichroic surface, the effective optical path length increases in each layer of the filter. The last point is decisive since the layer thickness of the layer is proportional to the desired shift of the wavelength. In other words, the edge sharpness of the filter decreases the thicker the resulting layer or the greater the resulting angle of incidence of an incident beam. However, a high edge sharpness is necessary to spectrally separate the incident light cleanly. If the edge sharpness is inadequate, light is partially lost or conducted into the incorrect imaging beam path. Since dichroic filters/mirrors involve a layer system, the errors of each individual layer add up, which makes the problem more severe. The invention offers an efficient solution for this purpose.

A nominal tilt angle of $\alpha=11.5°$ is set forth here as an example. In this case, the real spectrum of angles of incidence of the imaging beams incident on the first mirror surface of the prism can be between 8° and 15°. Relative path length differences of less than 1.5% can result therefrom. In contrast, if the tilt angle is $\alpha=22.5°$, which results in an optimum structural height of the prism, the angles of incidence can thus vary between, for example, 19° and 26°, which then results in more than 2.7% relative path length difference (this is approximately 80% more variation). This shows the importance of the tilt angle α.

The first wavelength range (which is recorded by the proximal image sensor) can be disjunct from the second wavelength range (which is recorded by the distal image sensor), thus in particular can display no overlap. This will be the case, for example, if the reflectance of the first mirror surface forms a short-pass filter characteristic (lower reflectance or higher transmittance for short wavelengths, higher reflectance or lower transmittance for long wavelengths) or long-pass filter characteristic or, for example, a bandpass filter or band-block filter characteristic.

The first wavelength range (acquired by the proximal image sensor) can be selected, for example, so that it is usable or is used for white light imaging and/or it covers the entire visible wavelength range. The second wavelength range (acquired by the distal image sensor), in contrast, can be outside the visible wavelength range or, for example, can only cover a partial range of the visible wavelength range. This procedure is useful in particular for fluorescent light imaging (for example using the distal image sensor) additionally to, in particular simultaneously with, white light imaging (for example using the proximal image sensor). Of course, these characteristics can also be formed in reverse with respect to the respective wavelength range (distal image sensor acquires approximately white broadband spectrum, proximal image sensor acquires further narrower spectrum). The invention additionally offers the advantage that both types of imaging in the two spectral ranges can each result in 3D images or stereoscopic images.

One of the two image sensors of the visualization system can be designed, for example, as a classic RGB sensor, for example to record white light images. The other image sensor can be designed, in particular in this case, for example, as a monochromatic image sensor, in particular in order to sensorially acquire a wavelength outside the visible spectrum, for example in the NIR or UV wavelength range.

As will become even better apparent on the basis of the figures, the second imaging beam path, after reflection on the first mirror surface, can be reflected again on a second mirror surface of the prism. This second mirror surface can be embodied in particular as an external mirror surface, for example by a metallization on the glass body of the prism. In this way, in particular the second imaging beam path can intersect the first imaging beam path. In other words, respective main beams of the two imaging beam paths can therefore intersect in an intersection point inside the prism. A situation can thus arise in which a beam reflected from the second mirror surface intersects the incident beam from which said reflected beam was branched off by means of the first mirror surface. With such an embodiment of the prism, reference is also made to "inward splitting", by which a compact embodiment of the optical system is enabled, because the optical path length of the second imaging beam path can be made correspondingly long by use of a double reflection.

The first mirror surface can be, for example, an internal mirror surface, namely, for example, if a glass body adjoins the first mirror surface of the prism without an air gap. The first reflection of the second imaging beam path can also be based in this case on an internal total reflection.

In general, it is advantageous if a surface normal of the proximal image sensor is aligned along a longitudinal axis of the visualization system (thus in particular of the above-mentioned endoscope) and if a second surface normal of the distal image sensor is transverse, thus in particular perpendicular, to the longitudinal axis. The respective surface normal is perpendicular here to the respective active surface of the image sensor. In particular an alignment of the surface normal of the distal image sensor perpendicular to the longitudinal axis results in a particularly compact structural form transverse to the longitudinal axis, since the "footprint" of the image sensor is in general very much larger than the usable active surface of the image sensor.

For a high image quality, it is moreover to be preferred if a respective optical path length of the main beams of the two imaging beam paths, measured from the entry surface of the prism up to a respective sensor surface of the proximal image sensor or the distal image sensor, is formed equally long. This applies in particular for the case when an imaging optical unit of the visualization system, which supplies the two imaging beam paths, is (optically) corrected for the first and second wavelength range (which are sensorially acquired by the distal or proximal sensor, respectively). The optical path lengths may be set, for example, by the selection of the glass material for the prism and the mentioned glass body and the geometrical dimensions thereof.

In an embodiment of the visualization system according to the invention alternative thereto, it can be provided that a respective optical path length of the main beams of the two imaging beam paths, again measured from the entry surface of the prism up to a respective sensor surface of the proximal image sensor or the distal image sensor, differs by an optical path length difference nΔL. This suggests itself in particular if an imaging optical unit of the visualization system, which supplies the two imaging beam paths, supplies different mean image-side focal lengths (back focal length=BFL) for the first and for the second wavelength range. It is apparent that it is advantageous in this case if the optical path length difference nΔL optically compensates for these focal length differences. In such an embodiment, the imaging optical unit is thus not intentionally corrected for the first and second wavelength range (in the meaning of a longitudinal chromatic aberration which is only very weakly pronounced for each of these wavelength ranges).

In particular in applications in which a large field of view (FOV) is to be observed using the visualization system, it is advantageous for a high imaging quality if the visualization system has an imaging optical unit which is upstream of the at least one prism and limits an angle spectrum of the second imaging beam path, with respect to a main beam, to +/−10°, preferably to +/−8°, particularly preferably to +/−6°. A field angle observable using the visualization system can in this case be at least 60°, preferably even at least 70° (for example, wide-angle endoscope). In particular a wide-angle objective can therefore be used in the visualization system, which is upstream from the imaging optical unit and reduces the field angle on the image side to an angle spectrum of imaging beams of <+/−20°, preferably to an angle spectrum of imaging beams of <+/−18°.

Due to the limiting of the angle spectrum of the second imaging beam path, the bandwidth of angles of incidence at which imaging beams of the second imaging beam path are incident on the first mirror surface can be limited, so that a sufficiently high reflectivity can always be ensured for all beams used for imaging (with respect to the distal image sensor). This is because the filter sharpness generally decreases strongly for excessively large angles of incidence. This is true in particular if a dichroic mirror is used, the reflectivity of which is typically strongly dependent on the angle of incidence of the incident light.

The mentioned imaging optical unit can in particular comprise the above-mentioned distal lens arrangements or the distal lens arrangement (which forms the two optical channels) or can be formed thereby.

The wide-angle objective can also comprise aspheric lenses in addition to a negative lens (concave lens). The imaging optical unit can also include aspheric lenses. It is moreover apparent that all of the lenses located in the respective imaging beam path (from the object up to the image sensor) cooperate in the imaging.

The invention will now be described in more detail on the basis of exemplary embodiments, but is not restricted to these exemplary embodiments. Further designs of the invention can be obtained from the following description of a preferred exemplary embodiment in conjunction with the general description, the claims, and the drawings.

BRIEF DESCRIPTION OF THE DRAWINGS

In the following description of various preferred embodiments of the invention, elements corresponding in their function receive corresponding reference numerals even with differing design or shaping.

In the figures.

DETAILED DESCRIPTION

Figure 1:
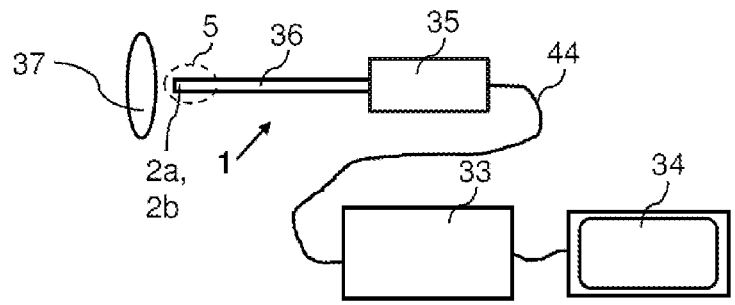
FIG. 1 shows a schematic view of a visualization system according to the invention.

FIG. 1 shows a visualization system 1 according to the invention in the form of a chip-in-tip endoscope, which includes a hand part 35 having an endoscope shaft 36 fastened thereon, which bears an optical assembly designed according to the invention in its distal end region 5, including two image sensors 2a and 2b arranged separately from one another. Using the endoscope 1, more precisely using the two image sensors 2a and 2b, images of the object 37 shown can be recorded in different spectral ranges. The recorded images are transferred here as a video signal to a camera control unit 33, which processes these signals and outputs them on a monitor 34.

Figure 2:
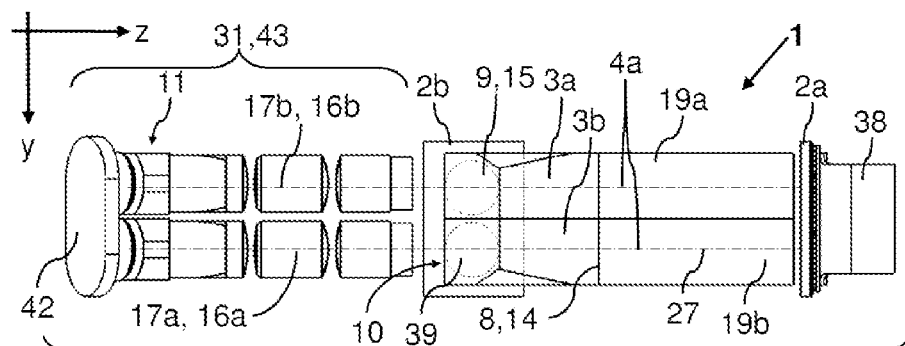
FIG. 2 shows a top view (counter to the x axis) of the distal end region of a visualization system according to the invention.

FIG. 2 shows a first example of how the optical elements of the endoscope 1 and the two image sensors 2a and 2b could be arranged according to the invention in the distal end region 5 of the endoscope 1. A front optical unit 11 of the endoscope 1 is visible, which already forms two optical channels 16a and 16b and together with downstream respective rod lenses (left lens arrangement 17a and right lens arrangement 17b) forms a respective first imaging beam path 4a. As shown by means of the two dot-dash lines, these two first imaging beam paths 4a extend parallel to one another and along the longitudinal axis 27 of the endoscope 1, which coincides with the longitudinal axis of the endoscope shaft 36. The two first imaging beam paths 4a enter a respective prism 3a and 3b through a distal entry surface 10, wherein each of these two prisms 3a and 3b deflects the respective first imaging beam path 4a onto the jointly used proximal image sensor 2a shown.

Figure 3:
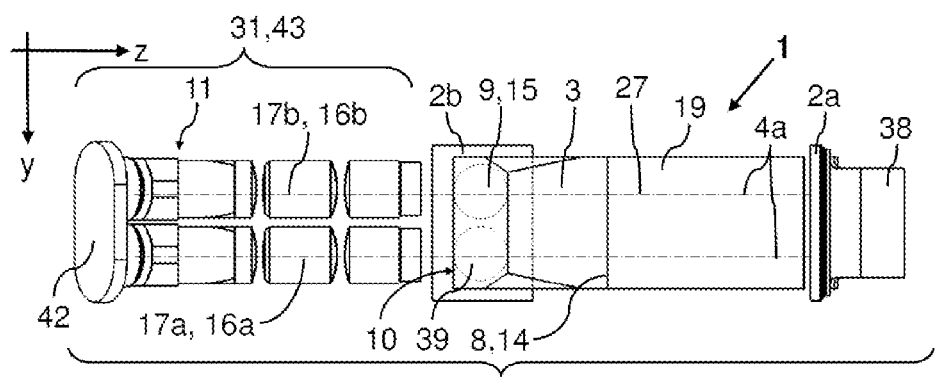
FIG. 3 shows a further top view from above of a second exemplary embodiment of a visualization system according to the invention, which differs from that of FIG. 2 due to the use of a common prism 3.
Figure 5:
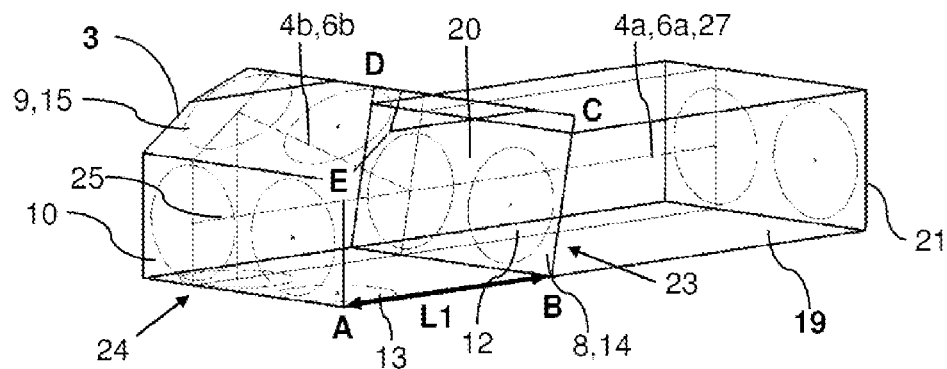
FIG. 5 shows a deflection prism designed according to the invention having a glass body connected thereto, wherein the prism could be used, for example, in the visualization system according to FIG. 3.

The exemplary embodiment according to FIG. 3 differs from that of FIG. 2 essentially in that instead of two separate prisms 3a and 3b, a common prism 3 is used here, which is illustrated in FIG. 5. It is to be noted in this case that the two prisms 3a and 3b in FIG. 2 are also designed in the same way as the prism of FIG. 5/FIG. 6, but having smaller lateral width.

Figure 4:
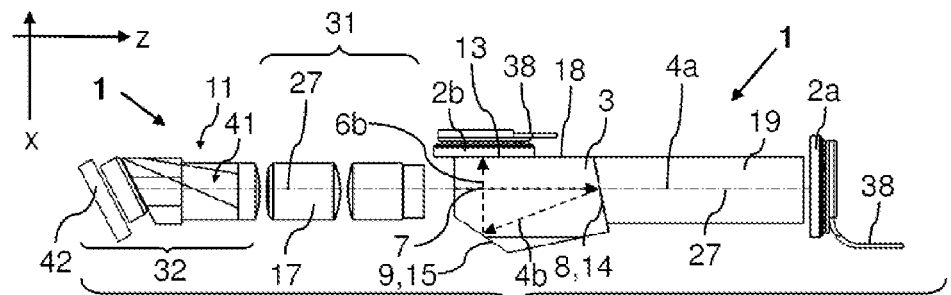
FIG. 4 shows the distal end region of a further visualization system designed according to the invention, wherein the viewing direction from the side is selected (counter to the y axis)

As will now be explained in more detail hereinafter, the respective prism 3 also deflects a second imaging beam path 4b onto a second distal image sensor 2b, which, as can be seen in FIGS. 2-4, is offset in the distal direction in relation to the proximal image sensor 2a. Accordingly, the distal image sensor 2b is actually closer to the upstream imaging optical unit 31 which is illustrated in FIGS. 2 and 3 and is formed there by means of an objective lens system 43 that comprises multiple optical lenses, in particular concave and convex lenses. To compensate for this, the second imaging beam path 4b is folded within the respective prism 3, more precisely deflected by two reflections, as can be seen well, for instance, in the side view of FIG. 4, but also in FIG. 6.

Figure 6:
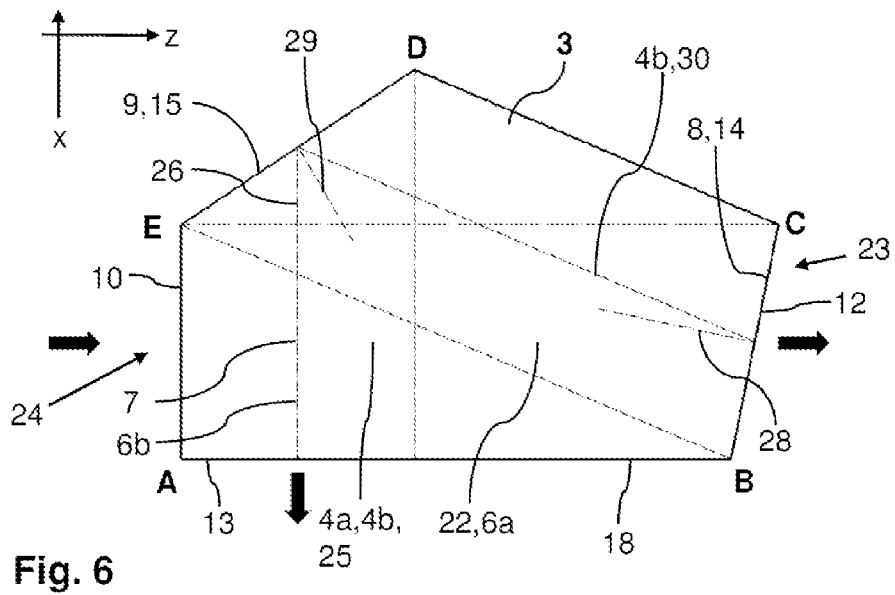
FIG. 6 shows the prism of FIG. 5 in a side view (counter to the y axis)

It can be seen well on the basis of FIGS. 5 and 6 that this second imaging beam path 4b also enters the respective prism 3 through the distal entry surface 10. However, this imaging beam path 4b is subsequently deflected by means of a first reflection 14 on a first mirror surface 8 of the prism 3, wherein this mirror surface 8 is made wavelength-selective. The mirror surface 8 thus transmits the first imaging beam path 4a, which only comprises wavelengths in a first wavelength range. The second imaging beam path 4b, in contrast, comprises a second wavelength range that deviates from the first wavelength range. The second imaging beam path 4b is reflected from the first mirror surface 8. This is an internal reflection in this case, as can be seen, for example, on the basis of the course of the imaging beam path 4b in FIG. 6, for example at the point of the surface normals 28 of this first (interior/internal) mirror surface 8 of the prism 3.

It can be seen well on the basis of FIG. 6 that as a result light which is incident on the left in the prism 3 thus exits from the prism 3 at two exit surfaces, namely the proximal exit surface 12 and the distal exit surface 13. For example, the mirror surface 8 can be designed so that fluorescent light exits from the prism 3 from the distal exit surface 13, while white light exits from the proximal exit surface 12.

For the second imaging beam path 4b, for this purpose the beam 30 reflected from the first mirror surface 8 is reflected again on a second mirror surface 9, which can be designed, for example, as an external mirror. The beam 26 reflected from this second mirror surface 9 thus extends transversely to the longitudinal axis 27 of the endoscope 1 and intersects (inside the prism 3) at the intersection point 7 the main beam 6a of the first imaging beam path 4a, which is incident on the first mirror surface 8. While the proximal exit surface 12 thus lies opposite to the distal entry surface 10 and is therefore arranged at the proximal end 23 of the prism 3, the distal exit surface 13 is located distally offset thereto on the base side 18 of the prism 3 (side AB in FIG. 6).

Figure 10:
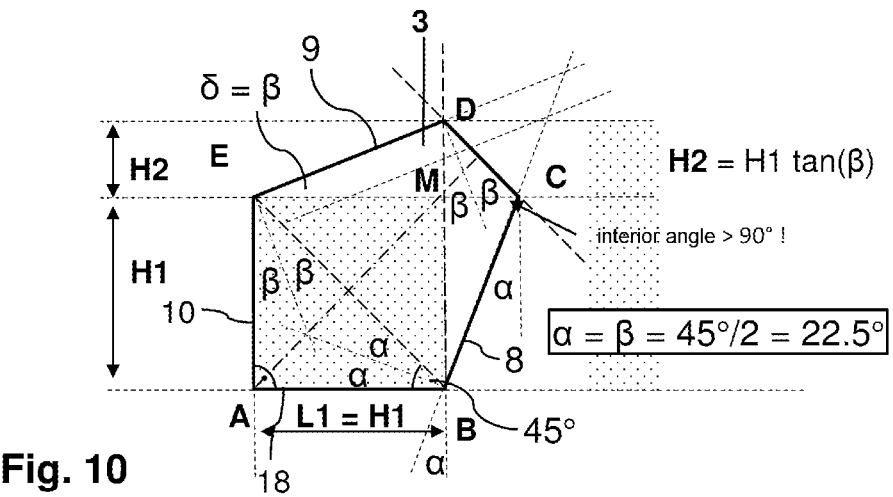
FIG. 10 shows an example of a deflection prism not according to the invention having optimally designed overall height H1+H2, wherein the two internal deflection angles α, 13 are selected to be equal.

As already mentioned in the general description and illustrated in FIG. 10, it is fundamentally favorable to tilt the first mirror surface 8, which is formed by the side BC of the prism 3, in relation to the longitudinal axis 27 or to the main beam 6a of the first imaging beam path 4a and at the same time likewise tilt the second mirror surface 9, which is formed by the side ED of the prism 3, correspondingly, so that the two deflection angles $\alpha$ and $\beta$ shown in FIG. 10 are just equal in size. This is because for the desired beam deflection, for which $2\alpha+2\beta=90°$ is to apply, accordingly $\alpha$ and $\beta$ have to be 22.5°. For this case, it can be shown relatively easily that the resulting overall height H1+H2 of the prism 3 (cf. FIG. 10) is minimal, in any case in consideration of the boundary condition that all of those beams which are reflected on the second mirror surface 9/the side ED of the prism 3 are to exit completely and unobstructed from the base side 18 (thus the side AB) of the prism 3.

It can be seen well on the basis of FIG. 10 that the resulting overall structural height H1+H2 of the prism will therefore be minimal for $\alpha=22.5°$ and at the same time it can be ensured at a length of the base side of L1=H1 that the beams reflected on the second mirror surface 9 do not strike the first mirror surface 8 again.

Figure 11:
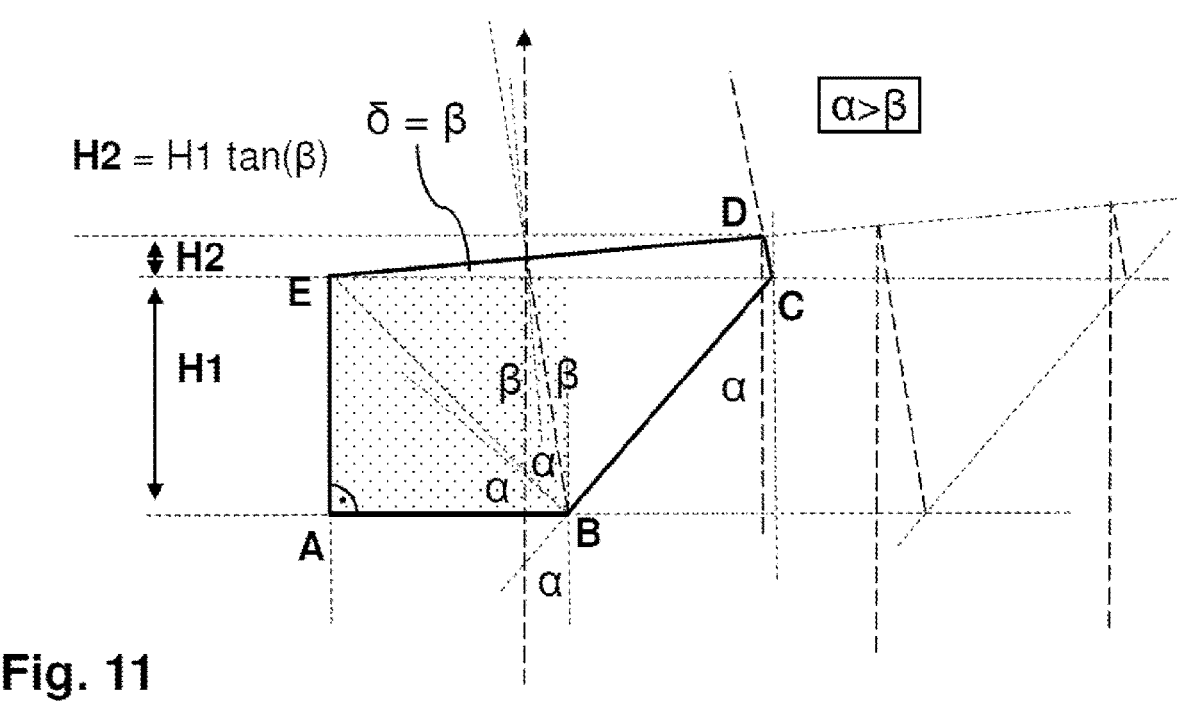
FIG. 11 shows, for the sake of completeness, a further example of a deflection prism, in which now the first tilt angle α is selected to be greater than the second deflection angle β, which results in an impractical shape of the prism, however.

As FIG. 11 shows, with further enlargement of the first tilt angle $\alpha$ (thus of the first deflection angle $\alpha$), the height H2 and thus the overall height H1+H2 of the prism 3 could be reduced, specifically for a predetermined height H1 of the distal entry window 10 (=side AE of the prism 3). In this case, however, all light beams which are reflected on the upper side ED of the prism 3 (=second reflection 15 of the second imaging beam path 4b) would no longer exit through the base side 18; rather, some of these light beams reflected on the second mirror surface 9 would (again) strike the first mirror surface 8 (thus the side BC) of the prism 3, which is to be avoided in particular.

Figure 8:
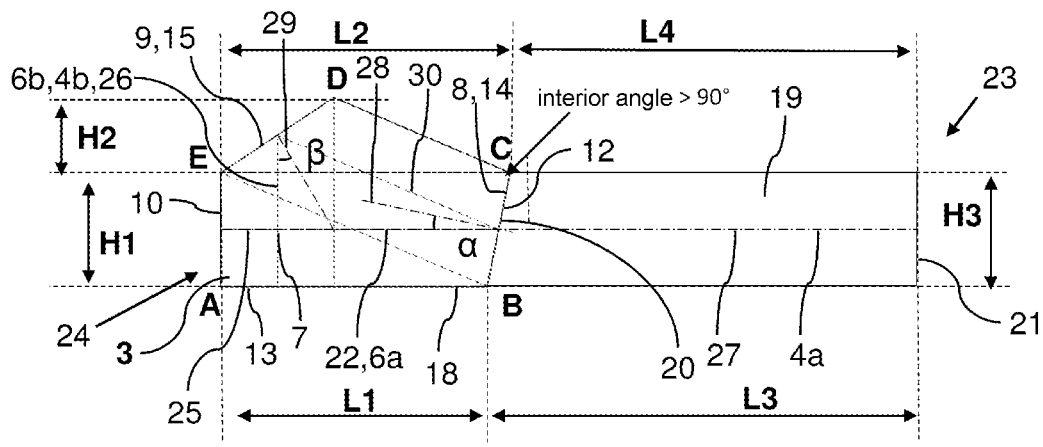
FIG. 8 shows a prism according to the invention similar to that of FIG. 5 or 6 having a glass body 19 placed thereon, wherein numerous geometric details are illustrated.
Figure 9:
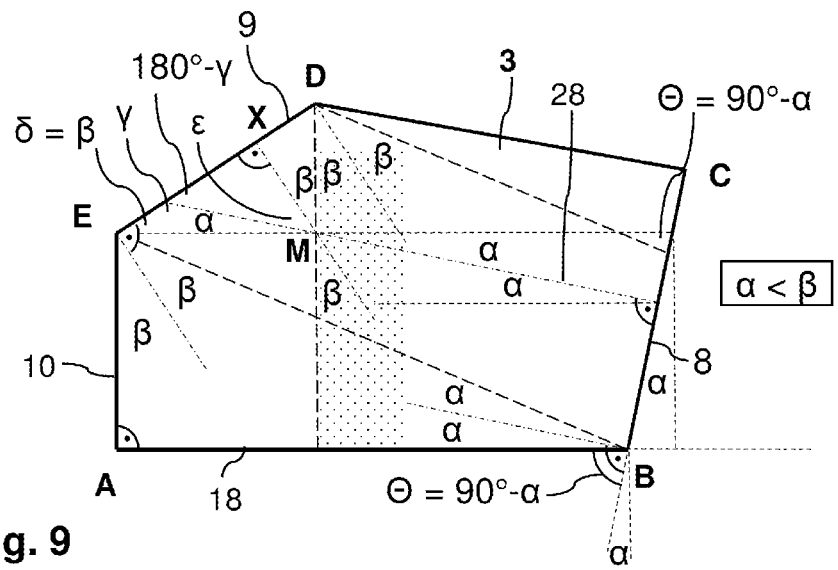
FIG. 9 shows an example of a deflection prism according to the invention, in which the tilt angle α is selected to be smaller than the deflection angle β of the second mirror surface.

The invention as defined in claim 1 and illustrated in FIG. 6 on the basis of the prism 3 therein deviates from the optimum design of the prism for the structural height as shown in FIG. 10, specifically in that it is intentionally accepted that the resulting height H2 (cf. FIG. 8) is greater than is actually geometrically necessary. This is achieved in that the base side 18 is selected to be somewhat longer than the height H1 of the entry window 10, so that for a ratio of the length L1 of this base side 18 (cf. FIG. 8) and a height H1 of the entry surface 10 of the prism 3, L1/H1>1.5 applies. A resulting tilt angle $\alpha$ of the first mirror surface 8 automatically results therefrom, which is smaller than said 22.5° as illustrated in FIG. 10.

Figure 7:
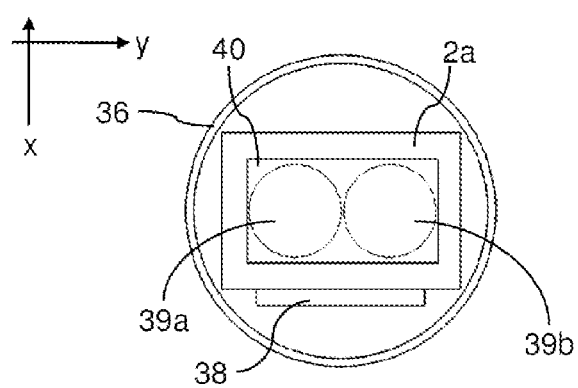
FIG. 7 shows a top view along the z axis/optical axis of a proximally arranged image sensor of a visualization system according to the invention, for example the proximal image sensor of the visualization system of FIGS. 2/3/4.

As can be seen well in particular on the basis of FIG. 4, the alignment of the surface normal of the distal image sensor 2b perpendicular to the longitudinal axis 27 of the endoscope 1 results in a particularly compact structural form transverse to this longitudinal axis 27, since the "footprint" of the image sensor 2b is generally very much larger than the usable active surface 40 of the image sensor 2a/2b. This can be seen well, for example, in the top view of the proximally arranged image sensor 2a in FIG. 7, in which the active image sensor surface 40 of the image sensor 2a and its external dimensions inside the installation space made available by the endoscope shaft 36 can be seen. Furthermore, it can be seen that the two optical channels 16a and 16b, which are already formed by the imaging optical unit 31 and are passed on by the prism 3, only illuminate respective circular imaging regions 39a and 39b on the rectangular image sensor surface 40 of the image sensor 2a. It is conceivable well here that 3D images or stereoscopic images can be recorded using this approach according to the invention, i.e., the image sensor 2a shown in FIG. 7 is configured for acquiring 3D images.

Moreover, it can be seen in FIGS. 2 and 3 on the basis of the circular imaging regions 39 therein of the distally arranged image sensor 2b therein, but also on the basis of the corresponding circles in FIG. 5, that stereoscopic images can thus be recorded in two different wavelength ranges. This is because the distal image sensor 2b sensorially acquires only those wavelengths which are reflected or deflected from the first mirror surface 8 of the prism 3, while the proximally arranged image sensor 2a only sensorially acquires those wavelengths which are transmitted by this first mirror surface 8. This can be seen well if one follows the two imaging beam paths 4a and 4b in FIG. 5 through the prism 3 and the glass body 19 adjoining thereon.

In all three exemplary embodiments shown in FIGS. 2-4, at least one prism 3, namely either the commonly used prism 3 or the respective assigned separate prism 3a/3b in the case of FIG. 2, each deflects one of the two optical channels 16a and 16b not only onto the proximal image sensor 2a but also onto the distal image sensor 2b. In other words, each of the two image sensors 2a and 2b therefore "sees" the observed object 37 both through the left optical channel 16a and through the right optical channel 16b, so that each of the two image sensors can supply 3D images.

The two optical channels 16a and 16b can be implemented here by jointly used optical elements or by separately arranged optical elements, such as the rod lenses shown in FIGS. 2 and 3. However, the function of the prism 3 is the same in all these cases, namely the prism 3 separates two different wavelength ranges with the aid of the wavelength-selective first mirror surface 8, so that these two wavelength ranges can each be sensorially acquired by the two image sensors 2a and 2b. The prism 3, more precisely the wavelength-selective mirror surface 8, thus acts as an optical beam splitter.

As already described above in detail, the tilt angle $\alpha$ is an important parameter in particular if the first mirror surface 8 is embodied as a dichroic filter, which influences the quality of the imaging that can still be achieved using the distal image sensor 2b. To avoid imaging errors here, it is favorable to select the tilt angle $\alpha$ to be comparatively small, such as <20° or even <15°. In this case, the dimension of the tilt angle $\alpha$ still permissible for optimum imaging is not least dependent on how large the bandwidth of wavelengths is which has to be deflected by the wavelength-selective mirror surface 8.

In addition, it is also important to avoid aberrations that imaging beams which enter the prism 3 through the distal entry surface 10 are only incident on the first mirror surface 8 at comparatively small angles of incidence. For this purpose, it is favorable as stated to select the tilt angle α to be small, thus to align the first mirror surface 8 comparatively steeply in relation to the longitudinal axis 27 of the endoscope 1.

At the same time, however, it is favorable for high imaging quality if the spectrum of incident angles is limited in any case. For this purpose, it is provided in particular, as can be seen, for example, in the exemplary embodiment of FIG. 4, to design the imaging optical unit 31 upstream of the prism 3 so that it limits an angle spectrum of the second imaging beam path 4b, in relation to a main beam 6a of the first imaging beam path 4a, to +/−10° or even smaller values. This works even if the visualization system 1 is designed, for example, as a wide-angle endoscope 1 having a wide-angle objective 32 which can observe a field angle of at least 60° or even at least 70°. Even if an oblique view is used, as in the example of FIG. 4, such a wide-angle objective 32 can still be designed so that it limits the angle spectrum of the imaging beams to at most+/−20° on the image side, which then represents the bandwidth of angles which are incident on the downstream imaging optical unit 31.

Finally, it is also to be noted that the respective optical path lengths of the main beams 6a and 6b of the two imaging beam paths 4a and 4b, each measured from the entry surface 10 of the prism 3 up to the respective sensor surface 40 of the respective image sensor 2a/2b, do not necessarily have to be formed approximately equal in length. The imaging optical unit 31 can thus supply, for example, two imaging beam paths 4a and 4b in the two different wavelength ranges which have a significant optical path length difference nΔL. This will be the case, for example, if the imaging optical unit 31 upstream of the prism 3 is in particular not optically corrected with a high level of effort for the two wavelength ranges and thus generates different mean image-side focal lengths (back focal length=BFL) for the first and second wavelength range. However, even in such a case, by way of corresponding dimensioning, for example of the rear glass body 19, not only the distal image sensor 2b but also the proximal image sensor 2a can be placed in the respective focal plane (which exists for the respective spectral range), so that sharp images can be recorded using each of the two image sensors 2a/2b, i.e., in both wavelength ranges.

In summary, for improved imaging in a visualization system 1, in particular a chip-in-tip endoscope 1, having two image sensors 2a and 2b, which are spaced apart from one another axially with respect to a longitudinal axis 27 of the visualization system 1 and sensorially acquire a respective imaging beam path 4a and 4b, which is generated by an assigned imaging optical unit 31 upstream from a deflection prism 3, it is provided that a structural height of the prism 3 be made suboptimal in order to thus be able to alleviate imaging errors upon use of a wavelength-selective first mirror surface 8 of the prism 3. Moreover, it is alternatively or additionally provided that two optical channels 16a and 16b be formed by means of the imaging optical unit 31 by which the image sensors 2a and 2b, preferably in different wavelength ranges, can each acquire images of an object 37 observed using the visualization system 1 from different perspectives.

LIST OF REFERENCE SIGNS 1 visualization system, in particular endoscope
2a (first) proximally arranged image sensor
2b (second) distally arranged image sensor
3 prism
4a first imaging beam path (ends in 2a)
4b second imaging beam path (ends in 2b)
5 distal end region (of 1)
6a main beam (of 4a)
6b main beam (of 4b)
7 intersection point (of 6a and 6b)
8 first, in particular internal, mirror surface (of 3)
9 second, in particular external, mirror surface (of 3)
10 distal entry surface (at the distal end of 3)
11 front optical unit
12 proximal exit surface (of 3, opposite to 10)
13 distal exit surface (of 3)
14 first reflection (of 4b)
15 second reflection (of 4b)
16a left optical channel
16b right optical channel
17a left lens arrangement (to form 16a)
17b right lens arrangement (to form 16b)
18 base side (of 3, on which 13 is formed)
19 glass body
20 entry surface (of 19)
21 exit surface (of 19)
22 optical axis (of 3 or 4a)
23 proximal end (of 3)
24 distal end (of 3)
25 incident beam (incident on 8)
26 reflected beam (reflected from 9)
27 longitudinal axis (of 1)
28 surface normal (of 8)
29 surface normal (of 9)
reflected beam (reflected from 8)
31 imaging optical unit
32 wide-angle objective
33 camera control unit
34 monitor
35 hand part
36 endoscope shaft
37 object
38 flex PCB
39 imaging region (on 2a/2b)
image sensor surface (=active surface of 2a/2b)
41 further prism
42 cover glass
43 objective lens system
44 video cable

The invention claimed is:

1. A visualization system (1), comprising:
a proximal image sensor (2a) and a distal image sensor (2b);
at least one prism (3), which deflects a first imaging beam path (4a) onto the proximal image sensor (2a) and a second imaging beam path (4b) onto the distal image sensor (2b);
the at least one prism (3) includes a wavelength-selective first mirror surface (8) by which the second imaging beam path (4b), after entering the at least one prism (3) through a distal entry surface (10), is deflected and exits from the at least one prism (3) from a distal exit surface (13), which is formed on a base side (18) of the at least one prism (3); and
for a ratio of a length L1 of the base side (18) and a height H1 of the entry surface (10), the following applies:

$$L1/H1 > 1.5.$$

2. The visualization system (1) according to claim 1, further comprising: a left optical channel (16a) and a right optical channel (16b) for generating 3D images;

the at least one prism (3) deflects one or both of the optical channels (16a, 16b) both onto the proximal image sensor (2a) and onto the distal image sensor (2b), such that using each of the proximal and distal image sensors (2a, 2b) at least one of 3D-images or stereoscopic images are recordable.

3. The visualization system (1) according to claim 2, wherein the stereoscopic images are recordable in two different wavelength ranges.

4. The visualization system (1) as claimed in claim 2, wherein two separate distal lens arrangements (17a, 17b) respectively form the left or right optical channel (16a, 16b).

5. The visualization system (1) as claimed in claim 2, wherein a common distal lens arrangement (17) forms both optical channels (16a, 16b).

6. The visualization system (1) as claimed in claim 2, wherein the at least one prism includes a common prism (3) for both of the optical channels (16a, 16b) respectively deflects the first imaging beam path (4a) onto the proximal image sensor (2a) and the second imaging beam path (4b) onto the distal image sensor (2b).

7. The visualization system (1) as claimed in claim 2, wherein the at least one prism comprises two prisms (3a, 3b) for one of the two optical channels (16a, 16b) in each case that respectively deflect the first imaging beam path (4a) onto the proximal image sensor (2a) and the second imaging beam path (4b) onto the distal image sensor (2b), to separate two different wavelength ranges from one another, which are each sensorially acquired by the two image sensors (2a, 2b).

8. The visualization system (1) as claimed in claim 1, wherein a surface normal (28) of the first mirror surface (8) encloses an angle α with an optical axis (22) of the first imaging beam path (4a), for which the following applies: $\alpha \leq 20°$.

9. The visualization system (1) as claimed in claim 1, wherein the proximal image sensor (2a) sensorially acquires a first wavelength range and the distal image sensor (2b) sensorially acquires a second wavelength range deviating from the first wavelength range.

10. The visualization system (1) as claimed in claim 9, wherein at least one of a) the first mirror surface (8) transmits the first wavelength range and reflects the second wavelength range, or the two image sensors (2a, 2b) a respective spectral sensitivity from one another.

11. The visualization system (1) as claimed in claim 1, wherein the second imaging beam path (4b), after reflection on the first mirror surface (8), is reflected again on a second mirror surface (9) of the at least one prism (3), such that the second imaging beam path (4b) intersects the first imaging beam path (4a).

12. The visualization system (1) as claimed in claim 11, wherein at least one of a) the first mirror surface (8) is an internal mirror surface, or b) the first reflection of the second imaging beam path (4b) is based on an internal total reflection.

13. The visualization system (1) as claimed in claim 1, wherein respective main beams (6a, 6b) of the two imaging beam paths (4a, 4b) intersect in an intersection point (7) within the at least one prism (3).

14. The visualization system (1) as claimed in claim 13, wherein a beam (26) reflected from a second mirror surface (9) of the at least one prism (3) intersects an incident beam (25) from which the reflected beam (26) was branched off by the first mirror surface (8).

15. The visualization system (1) as claimed in claim 1, wherein a surface normal of the proximal image sensor (2a) is aligned along a longitudinal axis (27) of the visualization system (1), and a second surface normal of the digital image sensor (2b) is transverse to the longitudinal axis (27).

16. The visualization system (1) as claimed in claim 1, wherein a respective optical path length of main beams (6a, 6b) of the two imaging beam paths (4a, 4b), measured from the entry surface (10) of the at least one prism (3) up to a respective sensor surface of the proximal image sensor (2a) or the distal image sensor (2b), is formed equal in length.

17. The visualization system (1) as claimed in claim 16, further corn p'rising an imaging optical unit (31) of the visualization system (1), which supplies the two imaging beam paths (4a, 4b), is corrected for a first and a second wavelength range.

18. The visualization system (1) as claimed in claim 17, wherein a respective optical path length of main beams (6a, 6b) of the two imaging beam paths (4a, 4b), measured from the entry surface (10) of the at least one prism (3) up to a respective sensor surface of the proximal image sensor (2a) or the distal image sensor (2b), differ by an optical path length difference $n\Delta L$, and the imaging optical unit (31) which supplies the two imaging beam paths (4a, 4b), supplies different mean image-side focal lengths for the first and second wavelength range, and the optical path length difference $n\Delta L$ optically compensates for said focal length differences.

19. The visualization system (1) as claimed in claim 1, further comprising an imaging optical unit (31) upstream of the at least one prism (3) that limits an angle spectrum of the second imaging beam path (4b) with respect to a main beam (6a) to +/−10°, wherein a field angle observable using the visualization system (1) is at least 60°, and wherein a wide-angle objective (32) upstream of the imaging optical unit (31) reduces the field angle on the image side to an angle spectrum of imaging beams of less than +/−20°.

20. The visualization system (1) as claimed in claim 1, wherein the visualization system comprises a chip-in-tip (CIT) endoscope.

* * * * *